US012187766B2

(12) United States Patent
Soundararajan et al.

(10) Patent No.: US 12,187,766 B2
(45) Date of Patent: Jan. 7, 2025

(54) COMPOSITIONS AND METHODS FOR TREATING SARS-CoV-2 INFECTIONS

(71) Applicant: nference, Inc., Cambridge, MA (US)

(72) Inventors: Venkataramanan Soundararajan, Andover, MA (US); Murali Aravamudan, Andover, MA (US); Arjun Puranik, San Jose, CA (US); Praveen Anand, Bangalore (IN); Aiveliagaram Venkatakrishnan, Cambridge, MA (US)

(73) Assignee: nference, Inc., Cambridge, MA (US)

( * ) Notice: Subject to any disclaimer, the term of this patent is extended or adjusted under 35 U.S.C. 154(b) by 0 days.

(21) Appl. No.: 17/734,653

(22) Filed: May 2, 2022

(65) Prior Publication Data

US 2022/0372082 A1     Nov. 24, 2022

Related U.S. Application Data

(60) Provisional application No. 63/183,140, filed on May 3, 2021.

(51) Int. Cl.
*C07K 16/40* (2006.01)
*A61P 31/12* (2006.01)
*C07K 14/005* (2006.01)

(52) U.S. Cl.
CPC ............ *C07K 14/005* (2013.01); *A61P 31/12* (2018.01); *C07K 16/40* (2013.01)

(58) Field of Classification Search
CPC ........ C07K 14/005; C07K 16/40; A61P 31/12
See application file for complete search history.

(56) References Cited

FOREIGN PATENT DOCUMENTS

| AU | 2005/334458 B9 | 6/2012 |
|---|---|---|
| WO | WO-2009/023306 A2 | 2/2009 |
| WO | WO-2022/235567 A1 | 11/2022 |

OTHER PUBLICATIONS

Pharynx (Throat) from Cleveland Clinic, pp. 1-9. Accessed Aug. 14, 2023. (Year: 2023).*
International Search Report and Written Opinion for International Application No. PCT/US22/27285 dated Aug. 26, 2022.

* cited by examiner

*Primary Examiner* — Julie Ha
(74) *Attorney, Agent, or Firm* — Caldwell Intellectual Property Law

(57) ABSTRACT

Methods for treating or reducing viral infection in a human subject, comprising administering to the subject a pharmaceutical composition comprising a protease inhibitor are described.

6 Claims, 8 Drawing Sheets

Specification includes a Sequence Listing.

Figure 1

ACE2

SCNN1A

SEQUENCE LISTING

```
<160> NUMBER OF SEQ ID NOS: 28

<210> SEQ ID NO 1
<211> LENGTH: 15
<212> TYPE: PRT
<213> ORGANISM: Homo sapiens

<400> SEQUENCE: 1

Gln Thr Asn Ser Pro Arg Arg Ala Arg Ser Val Ala Ser Gln Ser
1               5                   10                  15

<210> SEQ ID NO 2
<211> LENGTH: 11
<212> TYPE: PRT
<213> ORGANISM: Homo sapiens
```

```
<400> SEQUENCE: 2

Val Ser Leu Leu Arg Ser Thr Ser Gln Lys Ser
1               5                   10

<210> SEQ ID NO 3
<211> LENGTH: 8
<212> TYPE: PRT
<213> ORGANISM: Homo sapiens

<400> SEQUENCE: 3

Arg Arg Ala Arg Ser Val Ala Ser
1               5

<210> SEQ ID NO 4
<211> LENGTH: 8
<212> TYPE: PRT
<213> ORGANISM: Mus musculus

<400> SEQUENCE: 4

Arg Ser Ala Arg Ser Ala Ser Ser
1               5

<210> SEQ ID NO 5
<211> LENGTH: 8
<212> TYPE: PRT
<213> ORGANISM: Homo sapiens

<400> SEQUENCE: 5

Arg Arg Ala Arg Ser Val Val Ser
1               5

<210> SEQ ID NO 6
<211> LENGTH: 8
<212> TYPE: PRT
<213> ORGANISM: Homo sapiens

<400> SEQUENCE: 6

Arg Arg Val Arg Ser Val Ala Ser
1               5

<210> SEQ ID NO 7
<211> LENGTH: 8
<212> TYPE: PRT
<213> ORGANISM: Homo sapiens

<400> SEQUENCE: 7

Arg Arg Ala Arg Ser Val Ala Ile
1               5

<210> SEQ ID NO 8
<211> LENGTH: 8
<212> TYPE: PRT
<213> ORGANISM: Homo sapiens

<400> SEQUENCE: 8

Arg Arg Ala Arg Ser Ile Ala Ser
1               5

<210> SEQ ID NO 9
<211> LENGTH: 8
<212> TYPE: PRT
<213> ORGANISM: Homo sapiens
```

```
<400> SEQUENCE: 9

Arg Arg Ser Arg Ser Val Ala Ser
1               5

<210> SEQ ID NO 10
<211> LENGTH: 8
<212> TYPE: PRT
<213> ORGANISM: Homo sapiens

<400> SEQUENCE: 10

Arg Arg Ala Arg Ser Val Ser Ser
1               5

<210> SEQ ID NO 11
<211> LENGTH: 8
<212> TYPE: PRT
<213> ORGANISM: Homo sapiens

<400> SEQUENCE: 11

Arg Arg Ala Arg Ser Leu Ala Ser
1               5

<210> SEQ ID NO 12
<211> LENGTH: 8
<212> TYPE: PRT
<213> ORGANISM: Homo sapiens

<400> SEQUENCE: 12

Arg Leu Ala Arg Ser Val Ala Ser
1               5

<210> SEQ ID NO 13
<211> LENGTH: 8
<212> TYPE: PRT
<213> ORGANISM: Homo sapiens

<400> SEQUENCE: 13

Arg Trp Ala Arg Ser Val Ala Ser
1               5

<210> SEQ ID NO 14
<211> LENGTH: 8
<212> TYPE: PRT
<213> ORGANISM: Homo sapiens

<400> SEQUENCE: 14

Arg Gln Ala Arg Ser Val Ala Ser
1               5

<210> SEQ ID NO 15
<211> LENGTH: 8
<212> TYPE: PRT
<213> ORGANISM: Homo sapiens

<400> SEQUENCE: 15

Arg Arg Ala Arg Ser Val Ala Arg
1               5

<210> SEQ ID NO 16
<211> LENGTH: 8
<212> TYPE: PRT
<213> ORGANISM: Homo sapiens
```

<400> SEQUENCE: 16

Arg Arg Thr Arg Ser Val Ala Ser
1               5

<210> SEQ ID NO 17
<211> LENGTH: 8
<212> TYPE: PRT
<213> ORGANISM: Homo sapiens

<400> SEQUENCE: 17

Arg Arg Ala Arg Ser Val Thr Ser
1               5

<210> SEQ ID NO 18
<211> LENGTH: 8
<212> TYPE: PRT
<213> ORGANISM: Homo sapiens

<400> SEQUENCE: 18

Arg Arg Ala Arg Ser Val Ala Asn
1               5

<210> SEQ ID NO 19
<211> LENGTH: 8
<212> TYPE: PRT
<213> ORGANISM: Homo sapiens

<400> SEQUENCE: 19

Leu Arg Ala Arg Ser Val Ala Ser
1               5

<210> SEQ ID NO 20
<211> LENGTH: 8
<212> TYPE: PRT
<213> ORGANISM: Homo sapiens

<400> SEQUENCE: 20

Trp Arg Ala Arg Ser Val Ala Ser
1               5

<210> SEQ ID NO 21
<211> LENGTH: 8
<212> TYPE: PRT
<213> ORGANISM: Homo sapiens

<400> SEQUENCE: 21

Arg Arg Ala Arg Ser Val Ala Gly
1               5

<210> SEQ ID NO 22
<211> LENGTH: 8
<212> TYPE: PRT
<213> ORGANISM: Homo sapiens

<400> SEQUENCE: 22

Arg Arg Ala Arg Ser Val Ala Thr
1               5

<210> SEQ ID NO 23
<211> LENGTH: 8
<212> TYPE: PRT
<213> ORGANISM: Homo sapiens

```
<400> SEQUENCE: 23

Arg Arg Pro Arg Ser Val Ala Ser
1               5

<210> SEQ ID NO 24
<211> LENGTH: 8
<212> TYPE: PRT
<213> ORGANISM: Homo sapiens

<400> SEQUENCE: 24

Arg Arg Ala Arg Ser Ala Ala Ser
1               5

<210> SEQ ID NO 25
<211> LENGTH: 8
<212> TYPE: PRT
<213> ORGANISM: Homo sapiens

<400> SEQUENCE: 25

Gln Arg Ala Arg Ser Val Ala Ser
1               5

<210> SEQ ID NO 26
<211> LENGTH: 8
<212> TYPE: PRT
<213> ORGANISM: Homo sapiens

<400> SEQUENCE: 26

Arg Arg Ala Arg Ser Val Gly Ser
1               5

<210> SEQ ID NO 27
<211> LENGTH: 8
<212> TYPE: PRT
<213> ORGANISM: Homo sapiens

<400> SEQUENCE: 27

Arg Arg Ala Arg Ser Val Asp Ser
1               5

<210> SEQ ID NO 28
<211> LENGTH: 8
<212> TYPE: PRT
<213> ORGANISM: Homo sapiens

<400> SEQUENCE: 28

Arg Arg Ala Arg Gly Val Ala Ser
1               5
```

COMPOSITIONS AND METHODS FOR TREATING SARS-CoV-2 INFECTIONS

CROSS-REFERENCE TO RELATED APPLICATIONS

This application claims the benefit of U.S. Provisional Application No. 63/183,140, filed May 3, 2021, which is hereby incorporated by reference in its entirety.

Reference to Sequence Listing

This application contains a computer readable form of a Sequence Listing in ACSII text format under the title "1517-015USU1 Sequence Listing ST25_ST25," created on Aug. 6, 2024. The size of the ACSII text file is 4,279 bytes. The entirety of the ACSII text file is incorporated herein by reference.

BACKGROUND

Since the genome for severe acute respiratory syndrome coronavirus 2 (SARS-CoV-2) was released on Jan. 11, 2020, scientists raced to develop a vaccine.[1] However, vaccine development is a long and expensive process, at least in part because of evolutionary strategies adopted by viruses to evade immune surveillance and exploit host cell systems, e.g., molecular mimicry of host proteins. Accordingly, there is a long and unmet need for other treatment modalities for viral infection. Embodiments of the present disclosure relate to such methods of treatment, including at least in part, the identification and exploitation of molecular mimicry exhibited by viruses.

SUMMARY

The invention provided herein, relates, at least in part, on molecular mimicry of host proteins as used by viruses (.e.g., coronavirus, such as SARS-COV-2) for evasion of immune surveillance and to exploit host cell systems. The surface of SARS-COV-2 virions is coated with the spike(S) glycoprotein, whose proteolysis is key to the infection lifecycle. After the initial interaction of the S-protein with the ACE2 receptor', host cell entry is mediated by two key proteolytic steps. The S1 subunit of the S-protein engages ACE2, and viral entry into the host cell is facilitated by proteases that catalyze S1/S2 cleavage[2,3] at Arginine-667/Serine-668 (FIG. 1A). This is followed by S2' site cleavage that is required for fusion of viral-host cell membranes[1]. Disclosed herein is a unique S1/S2 cleavage site (RRARSVAS (SEQ ID NO: 3 absent in any previous coronavirus sequenced, that results in mimicry of an identical FURIN-cleavable peptide on the human epithelial sodium channel α-subunit (ENaC-α). Genetic truncation at this ENaC-α, cleavage site causes aldosterone dysregulation in patients, highlighting the functional importance of the mimicked SARS-COV-2 peptide.

In some aspects of the invention, disclosed herein are methods of treating or reducing viral infection in a human subject, comprising administering to the subject a pharmaceutical composition comprising a protease inhibitor.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

BRIEF DESCRIPTION OF THE DRAWINGS

Figure 1:
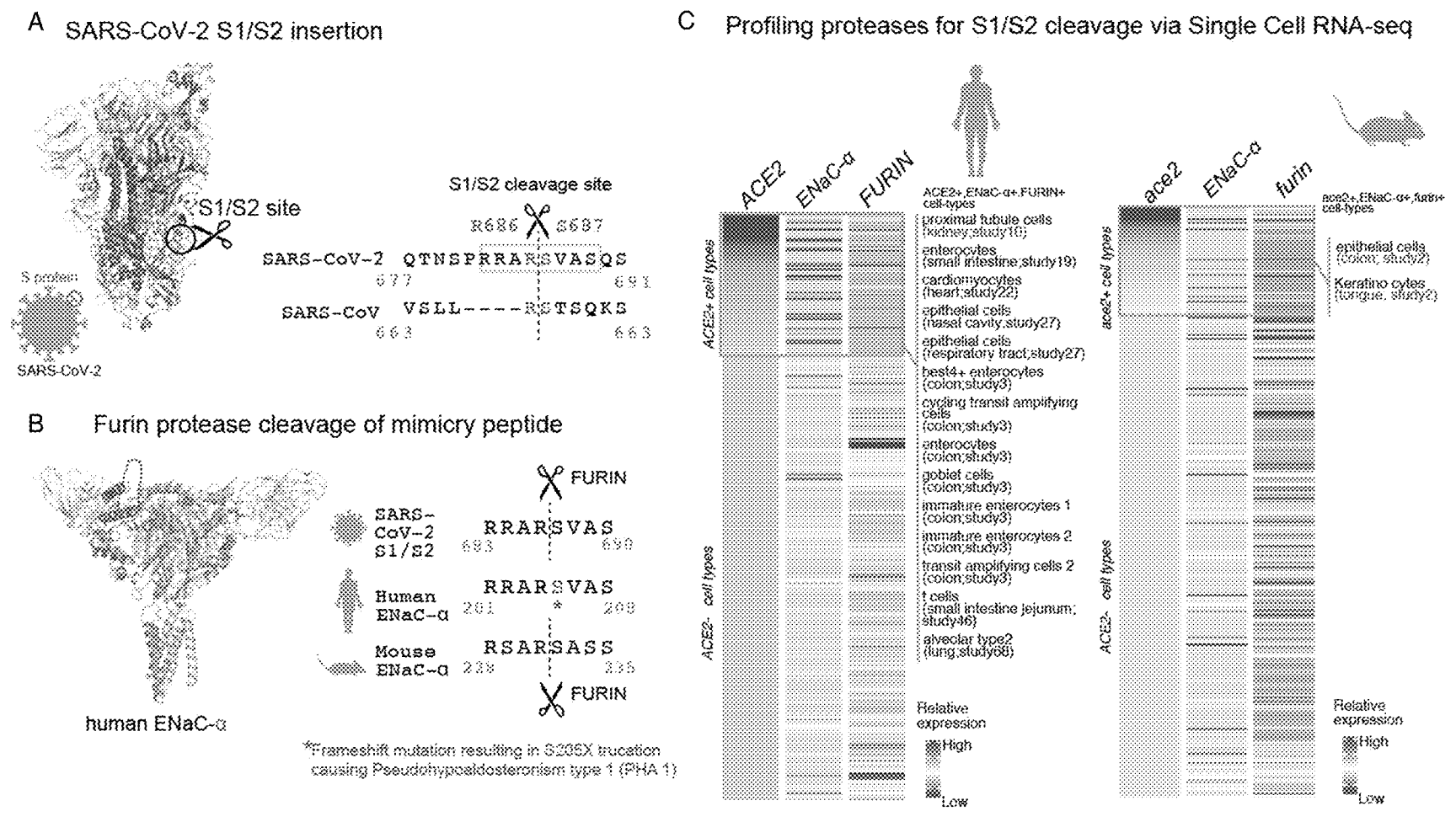

FIG. 1A-C depicts targeted molecular mimicry by SARS-COV-2 of human ENaC-α and profiling ACE2-FURIN-ENaC-α co-expression. (A) The cartoon representation of the S-protein homotrimer from SARS-COV-2 is shown (PDB ID: 6VSB). One of the monomers in highlighted red. The pairwise alignment of the S1/S2 cleavage site required for the activation of SARS (SEQ ID NO.: 2) and SARS-COV-2 (SEQ ID NO: 1) is depicted. The 4 amino acid insertion evolved by SARS-COV-2, along with the abutting cleavage site is shown in a box. (B) The cartoon representation of human ENaC protein is depicted (PDB ID: 6BQN; chain in green), highlighting the ENaC-α chain in green. The alignment on the right captures FURIN cleavage at the S1/S2 site of SARS-COV-2, along with its striking molecular mimicry of the identical peptide from human ENaC-α protein (RRARSVAS (SEQ ID NO.: 3) (circled in the cartoon rendering of human ENaC). The alignment also shows the equivalent 8-mer peptide of mouse ENaC-α (RSARSASS (SEQ ID NO.: 4)) that is also known to be cleaved by FURIN. (C) The single cell transcriptomic co-expression of ACE2, ENaC-α, and FURIN is summarized. The heatmap depicts the mean relative expression of each gene across the identified cell populations. The human and mouse single cell RNA-seq are visualized independently. The cell types are ranked based on decreasing expression of ACE2. The box highlights the ACE2 positive cell types in mouse and human samples.

DETAILED DESCRIPTION

Figure 2:
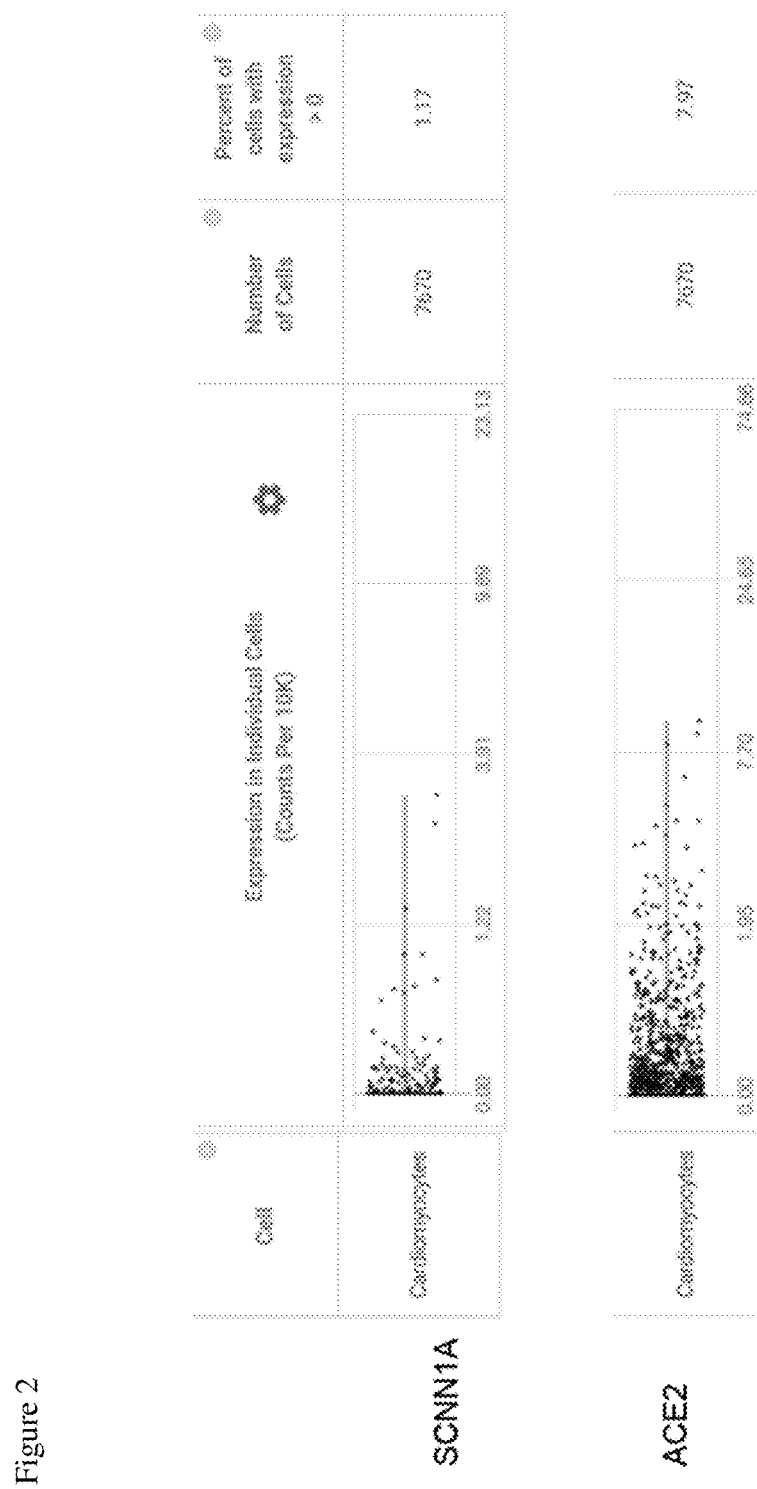
FIG. 2 shows expression of ENaC-α (SCNN1A) and ACE2 in cardiomyocytes (Primary data processed from Pubmed ID:31915373 and hosted on academia.nferx.com).
Figure 3:
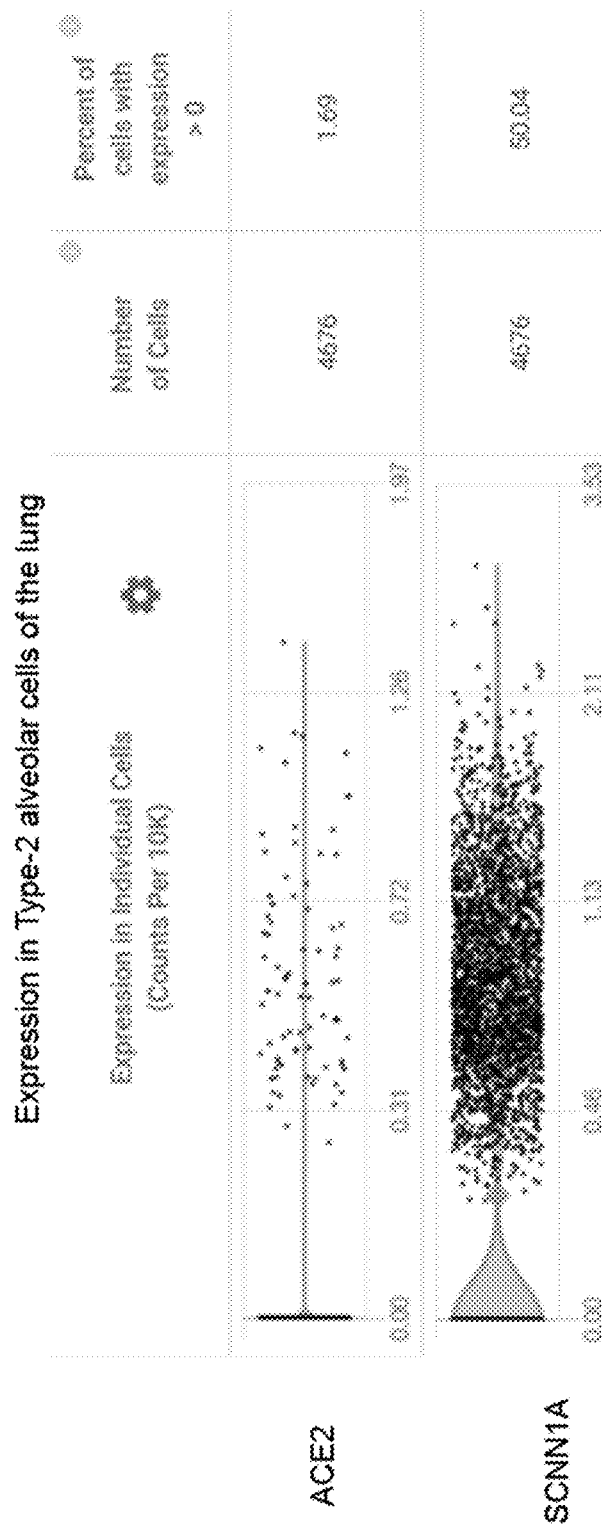
FIG. 3 shows expression of ENaC-α (SCNN1A) and ACE2 in Alveolar Cells of the lungs (Primary data processed from Pubmed ID: 31892341 and hosted on academia.nferx.com/).
Figure 4:
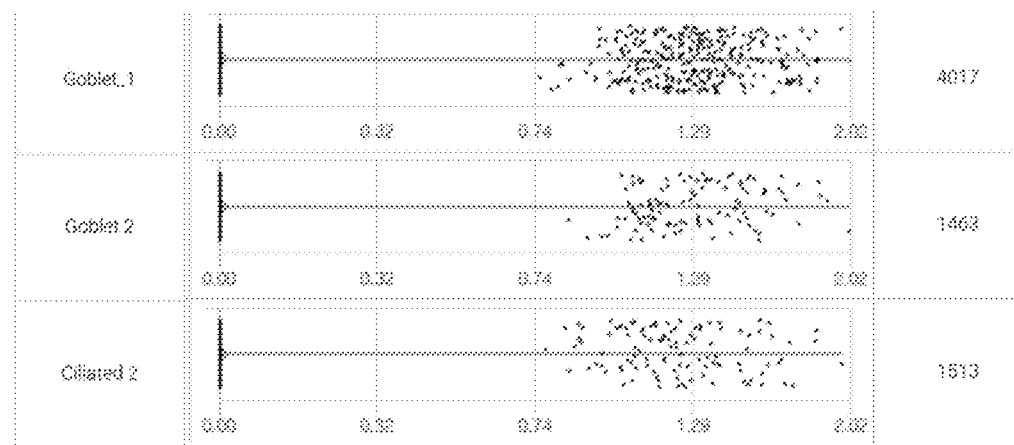
FIG. 4 shows expression of SCNN1A (ENaC-α) and ACE2 in Goblet cells and Ciliated cells of the nasal epithelial layer (Primary data processed from Pubmed ID: 32327758 and hosted on academia.nferx.com).
Figure 4:
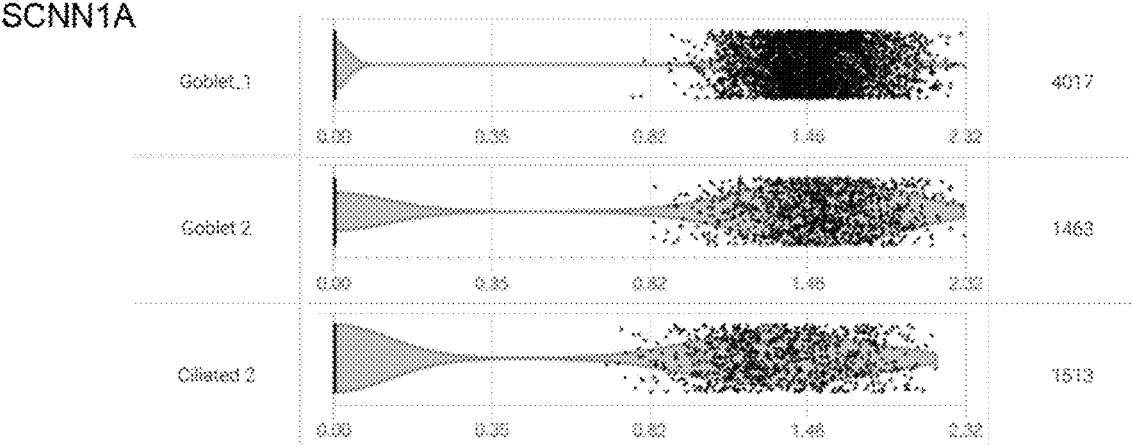
Figure 5:
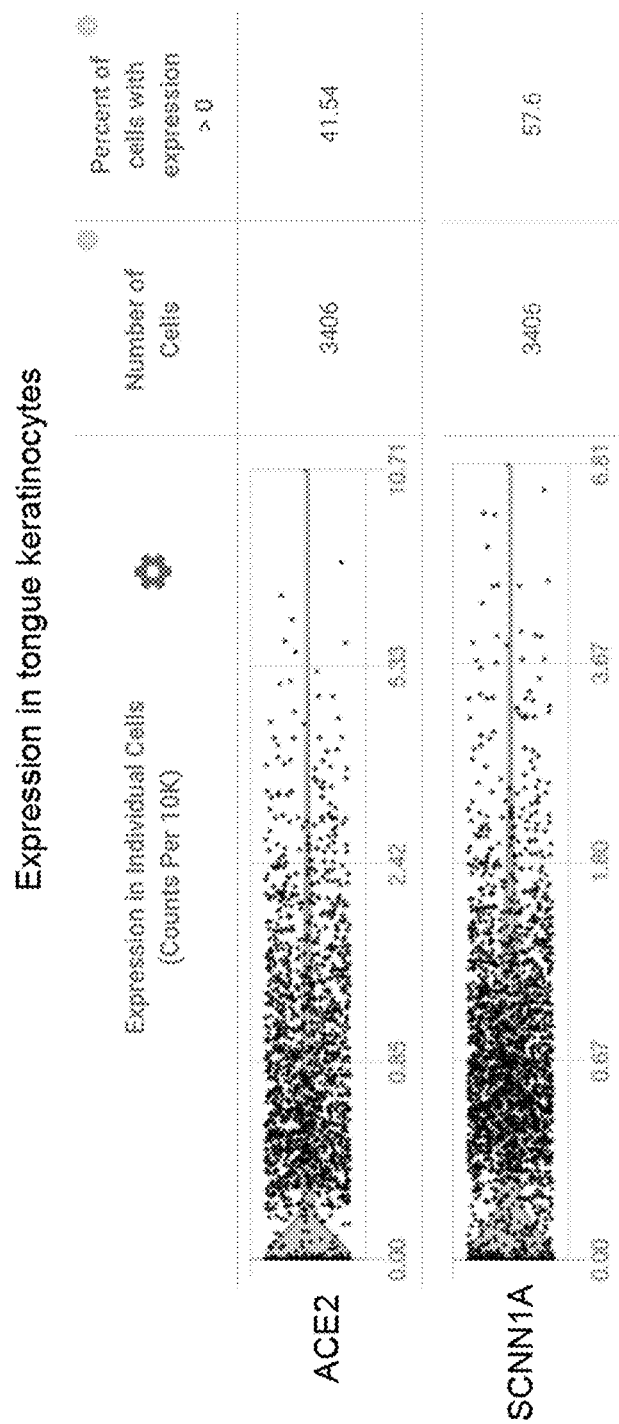
FIG. 5 shows expression of SCNN1A (ENaC-α) and ACE2 in Tongue keratinocytes (Primary data processed from Pubmed ID:30283141 and hosted on academia.nferx.com).
Figure 6:
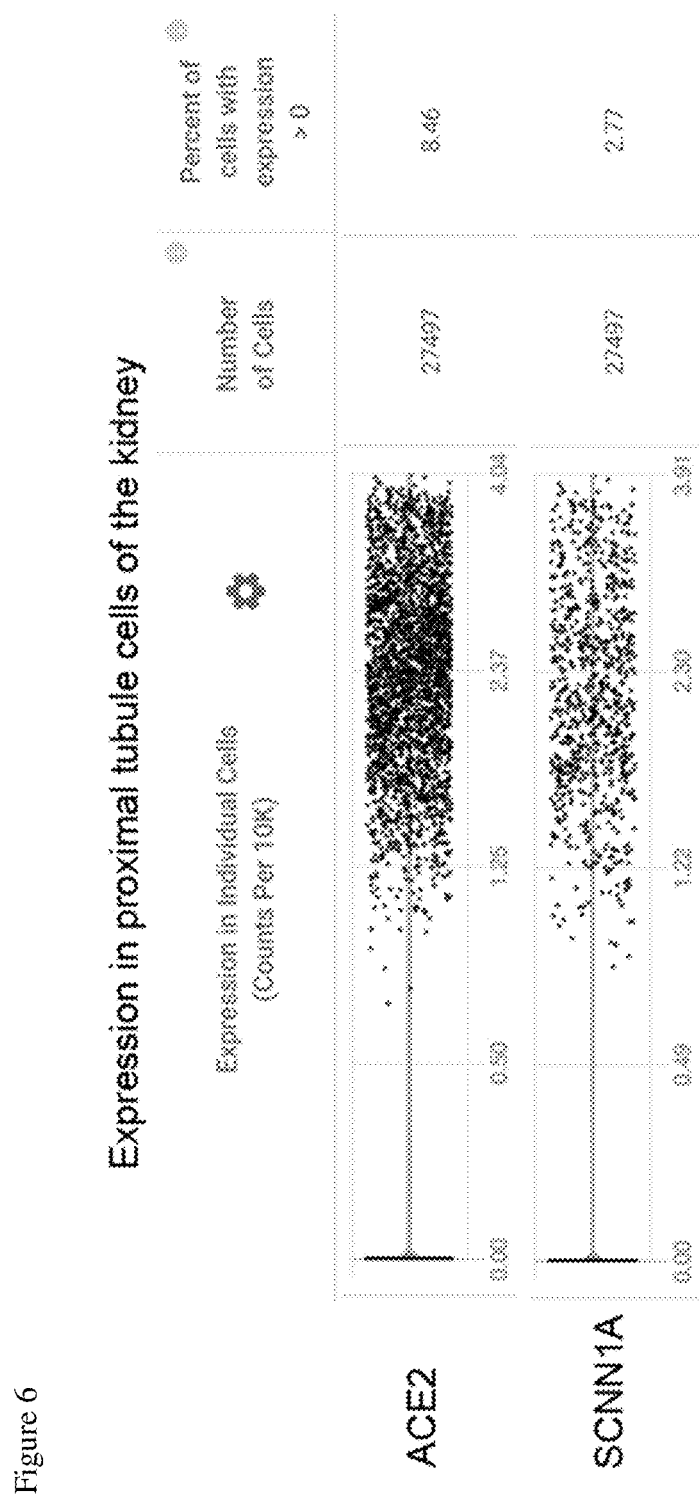
FIG. 6 shows expression of SCNN1A (ENaC-α) and ACE2 in Kidney proximal tubule cells (Primary data processed from Pubmed ID: 31604275 and hosted on academia.nferx.com).
Figure 7:
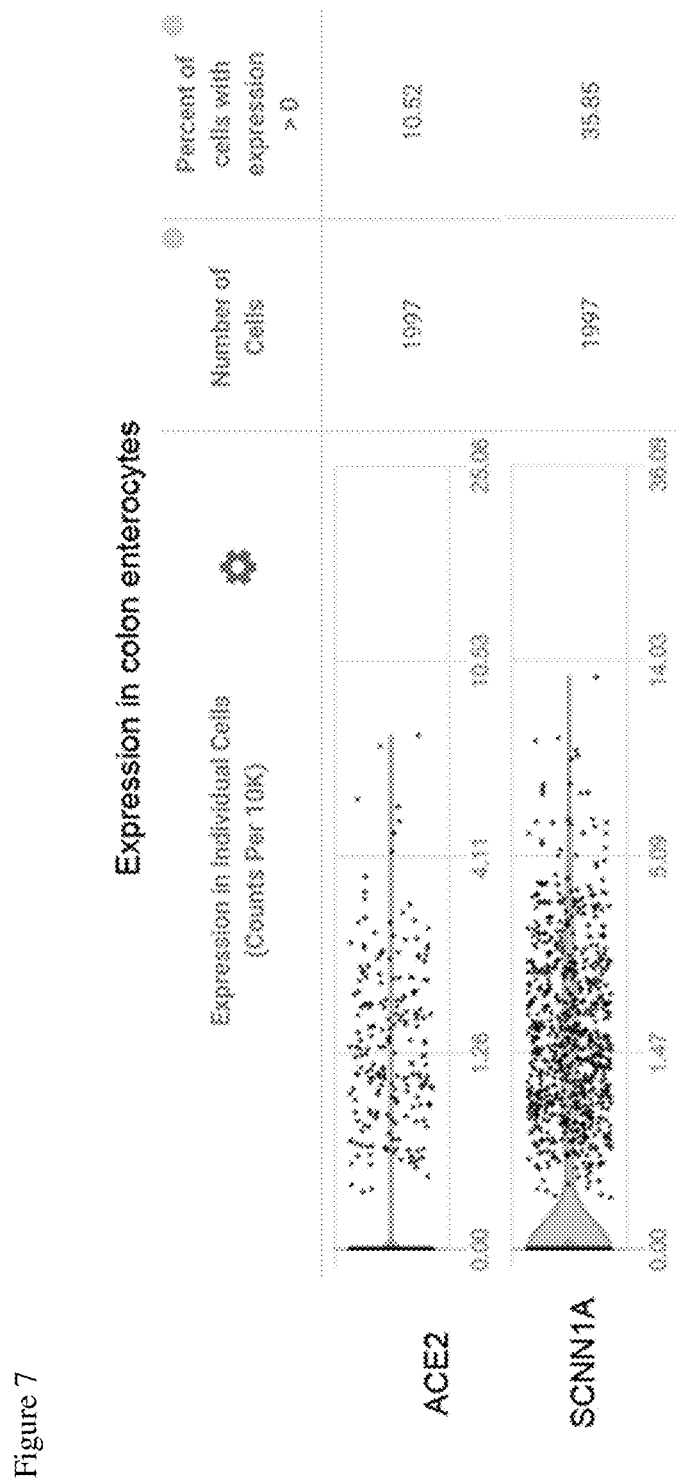
FIG. 7 shows expression of SCNN1A (ENaC-α) and ACE2 in Colon enterocytes (Primary data processed from Pubmed ID: 31348891 and hosted on academia.nferx.com).

As provided herein, single cell RNA-sect from 65 studies showed significant overlap between the expression of ENaC-α, and ACE2, the putative receptor for the virus, in cell types linked to the cardiovascular-renal-pulmonary pathophysiology of COVID-19. Triangulating this cellular fingerprint with amino acid cleavage signatures of 178 human proteases showed the potential for tissue-specific proteolytic degeneracy wired into the SARS-CoV-2 lifecycle. Thus, the evolution of SARS-CoV-2 into a global pandemic may be in part due to targeted mimicry of human ENaC and hijack of the associated host proteolytic network.

Aspects of the invention disclosed herein include methods of treating or reducing viral infection in a human subject, comprising administering to the subject a pharmaceutical composition comprising a protease inhibitor. In some aspects, provided herein are methods that can be used to reduce infectivity of a viral particle, e.g., reducing propagation of the virus particle; reducing release of the virus particle from a cell; and preferably reducing entry of the virus particle into a cell.

In some embodiments, the pharmaceutical composition comprises an inhibitor of one or more proteases selected from Furin, Proprotein Convertase Subtilisin/Kexin Type 2 (PCSK2), Proprotein Convertase Subtilisin/Kexin Type 4 (PCSK-4), Proprotein Convertase Subtilisin/Kexin Type 5 (PCSK-5), Proprotein Convertase Subtilisin/Kexin Type 6 (PCSK-6), Proprotein Convertase Subtilisin/Kexin Type 7 (PCSK-7), Plasminogen (PLG), or any combination thereof. In some such embodiments, the composition is administered to the subject directly to an organ selected from lung, small intestine, large intestine, pancreas, kidney, heart, or tongue. Said composition may be administered subcutaneously, intravenously, intramuscularly, intranasally, by inhalation, orally, sublingually, by buccal administration, topically, transdermally, or transmucosally, as are known in the art. For example, and without limitation, the composition is administered to the subject directly to the nasopharynx and/or the oropharynx. In preferred embodiments, the subject is suffering from SARS-COV-2 infection.

As used herein, the expression "treating or reducing viral infection" means improving, reducing, or alleviating at least one symptom or biological consequence of virus infection in a subject, and/or reducing or decreasing virus titer, load, replication or proliferation in a subject following exposure to a virus. The expression "treating or reducing viral infection" also includes shortening the time period during which a subject exhibits at least one symptom or biological consequence of the infection. Methods for treating virus infection, according to the present invention, comprise administering a pharmaceutical composition of the present invention to a subject after the subject is infected with the virus and/or after the subject exhibits or is diagnosed with one or more symptoms or biological consequences of virus infection. Preferably, the virus is a coronavirus such as SARS-CoV, or variants thereof. More preferably the virus is SARS-CoV-2.

As will be appreciated by those of skill in the relevant art, the symptom or biological consequence of virus infection will depend on the infecting viral particle. As a non-limiting example, SARS-CoV infection may include one or more of nasal congestion, sinus congestion, runny nose, sneezing, body (muscle) ache, head ache, chills, fever, cough, sore throat, fatigue, ear ache, or a diagnostic indicator of infection, e.g., detection of SARS-CoV by viral culture, hemagglutinin agglutination inhibition (HAI) assay, immunofluorescence, or nucleic acid-based detection (e.g., RT-PCR) using an appropriate specimen (e.g., nasal swab, nasopharyngeal swab, throat swab, endotracheal aspirate, sputum, bronchial wash, etc.). Thus, a subject who tests positive for infection by a diagnostic assay is considered a subject exhibiting a "symptom or biological consequence" of said virus infection.

As used herein, a "subject" shall mean a vertebrate animal including but not limited to a human, non-human primate, mouse, rat, guinea pig, rabbit, cow, dog, cat, horse, goat, bird, reptile, or fish. In some embodiments of the invention, a subject is a mammal. In some embodiments, the subject may be a domesticated animal, a wild animal, or an agricultural animal. Thus, the invention can be used to inhibit virus particle infectivity and to treat or reduce viral infection in human and non-human subjects. For instance, methods and compositions of the invention can be used in veterinary applications (for examples in zoos, reserves, farms, in the wild, etc.) as well as in human treatment regimens. In some embodiments of the invention, the subject is a human. In some embodiments of the invention, a subject is at risk of having, or has a viral infection.

The treatment approaches disclosed herein take advantage of the molecular mimicry exhibited by viruses as a strategy to evade immune surveillance and exploit mechanisms of the host cell to maintain or increase infectivity. The investigation of targeted mimicry of host proteins lead to the discovery that viruses may selectively hijack the host proteolytic network, which may represent therapeutic targets. Thus, disclosed herein are agents that target the activity a target protease (e.g., protease inhibitors). Without being bound by any particular theory, such agents/inhibitors include chemical compounds, small molecules, mixtures of chemical compounds and/or a biological macromolecules (such nucleic acids, antibodies, antibody fragments, proteins or a peptides). Moreover, the agents contemplated herein include those known in the art, and those that may be identified by screening or validation assays known in the art.

In some embodiments, the agent is an antibody or antibody fragment that binds specifically to the protease of interest. In some embodiments, the antibody depletes, neutralizes, or inhibits one or more associated activities of said protease.

In some embodiments, the inhibitor is an interfering nucleic acid specific for an mRNA product of a target gene encoding the protease. Such interfering nucleic acids are known in the art and include, without limitation, siRNAs, shRNAs, miRNAs, peptide nucleic acids (PNAs), and the like, as are known in the art.

Without being bound by any particular theory or methodology, a combination of agents may be administered to the subject in need thereof. The combination and administration of such agents may be informed, at least in part, by the methods disclosed herein. In some such embodiments, the combination of agents can be administered either in the same formulation or in separate formulations, either concomitantly or sequentially. Thus, a subject who receives such personalized treatment can benefit from a combined effect of different therapeutic agents.

In some embodiments, the agent (e.g., protease inhibitor), or combination of agents, is administered with a vaccine composition. The agent, or agents, may be administered either in the same formulation as the vaccine or in separate formulations, either concomitantly or sequentially. For example, in some embodiments, the protease inhibitor is administered to a vaccinated subject, or is administered prior to vaccination of a subject.

It will be appreciated by those of ordinary skill in the art that evaluation of a treatment, e.g., evaluation of the symptoms or clinical end-points of a viral infection, can be used in conjunction with methods of the invention to assess the status of a viral infection and/or the efficacy of a treatment for a viral infection.

EXAMPLES

Example 1: Analysis of SARS-CoV Variants

Comparing SARS-CoV-2 with SARS-CoV shows that the former has acquired a distinctive sequence insertion at the S1/S2 site (FIG. 1A). The resulting tribasic 8-mer peptide (RRARSVAS) on the SARS-CoV-2 S1/S2 site is conserved among 10,956 of 10,967 circulating strains deposited at GISAID[4], as of Feb. 6, 2022 (Table 1). This peptide is also absent in over 13,000 non-COVID-19 coronavirus S-proteins from the VIPR database[5]. Examining over 10 million peptides (8-mers) of 20,350 canonical human proteins from UniProtKB shows that the peptide of interest (RRARSVAS) is present exclusively in human ENaC-α, also known as SCNN1A (p-value=4E-4). The location of this SARS-CoV-2 mimicked peptide in the ENaC-α structure is in the extracellular domain (FIG. 1B).

Incorporated herein by reference is a sequence listing pdf file entitled, "1517-015USU1 sequence listing.pdf." created on Oct. 20, 2023, and including a size of 373 KB (381,456 bytes).

TABLE 1

SARS-CoV-2 variants in the RRARSVAS 8-mer peptide from 7,923,863 spike (S) protein sequences of the GISAID database. The specific variations are underlined.

| Variation in the mimicked 8-mer of interest (RRARSVAS) | Number of occurrences in the SARS-CoV-2 S-protein sequences | No. of unique PANGO lineages (GISAID) |
|---|---|---|
| RRARSVAS (SEQ ID NO: 3) | 7,564,445 | 1,575 |
| RRARSVVS (SEQ ID NO: 5) | 23,463 | 389 |
| RRVRSVAS (SEQ ID NO: 6) | 5,192 | 219 |
| RRARSVAI (SEQ ID NO: 7) | 3,767 | 157 |
| RRARSIAS (SEQ ID NO: 8) | 1,509 | 77 |
| RRSRSVAS (SEQ ID NO: 9) | 1,505 | 106 |
| RRARSVSS (SEQ ID NO: 10) | 1,362 | 131 |
| RRARSLAS (SEQ ID NO: 11) | 1,292 | 60 |
| RLARSVAS (SEQ ID NO: 12) | 1,272 | 114 |
| RWARSVAS (SEQ ID NO: 13) | 1,212 | 125 |
| RQARSVAS (SEQ ID NO: 14) | 912 | 86 |
| RRARSVAR (SEQ ID NO: 15) | 851 | 44 |
| RRTRSVAS (SEQ ID NO: 16) | 827 | 81 |
| RRARSVTS (SEQ ID NO: 17) | 705 | 54 |
| RRARSVAN (SEQ ID NO: 18) | 362 | 35 |
| LRARSVAS (SEQ ID NO: 19) | 207 | 53 |
| WRARSVAS (SEQ ID NO: 20) | 161 | 50 |

TABLE 1-continued

SARS-CoV-2 variants in the RRARSVAS 8-mer peptide from 7,923,863 spike (S) protein sequences of the GISAID database. The specific variations are underlined.

| Variation in the mimicked 8-mer of interest (RRARSVAS) | Number of occurrences in the SARS-CoV-2 S-protein sequences | No. of unique PANGO lineages (GISAID) |
|---|---|---|
| RRARSVAG (SEQ ID NO: 21) | 157 | 28 |
| RRARSVAT (SEQ ID NO: 22) | 91 | 17 |
| RRPRSVAS (SEQ ID NO: 23) | 83 | 16 |
| RRARSAAS (SEQ ID NO: 24) | 75 | 19 |
| QRARSVAS (SEQ ID NO: 25) | 67 | 22 |
| RRARSVGS (SEQ ID NO: 26) | 65 | 18 |
| RRARSVDS (SEQ ID NO: 27) | 64 | 23 |
| RRARGVAS (SEQ ID NO: 28) | 58 | 20 |
| [RLWQ][RLWQ][AVTP]R[SG][VILA][AVSTGD][SIRNGT] | 7609704 | 1577 |

ENaC regulates Na+ and water homeostasis and its expression levels are controlled by aldosterone and the associated Renin-Angiotensin-Aldosterone System (RAAS)[6]. Similar to SARS-CoV2, ENaC-α needs to be proteolytically activated for its function[7]. FURIN cleaves the equivalent peptide on mouse ENaC-α between the Arginine and Serine residues in the $4^{th}$ and $5^{th}$ positions respectively (RSARISASS)[8,9], akin to the recent report establishing FURIN cleavage at the S1/S2 site of SARS-CoV-2 (FIG. 1B)[1]. Furthermore, a frameshift mutation leading to a premature stop codon in Serine-205 at the $5^{th}$ position of the ENaC-α mimicked peptide (RRAR|SVAS) is known to cause the monogenic disease Pseudohypoaldosteronism type 1 (PHA1)[10]. This emphasizes the functional salience of the 8-mer peptide being mimicked by SARS-CoV-2.

Mimicry of human ENaC-α by the S1/S2 site suggests that SARS-CoV-2 is hijacking the protease network of ENaC-α for viral activation. An overlap between putative SARS-CoV-2 infecting cells and ENaC-α expressing cells was observed. Systematic single cell expression profiling of the ACE2 receptor and ENaC-α was performed across human and mouse samples comprising ~1.3 million cells (FIG. 1C)[11]. Notably, ENaC-α is expressed in the nasal epithelial cells, type II alveolar cells of the lung, tongue keratinocytes, and colon enterocytes (FIG. 1C and FIGS. 2-7), which are all implicated in COVID-19 pathophysiology[11,12]. Further, ACE2 and ENaC-α are known to be expressed generally in the apical membranes of polarized epithelial cells[13,14]. Such overlap of cell-types expressing ACE2 and ENaC-α, and similar spatial distributions at the apical surfaces, indicate that SARS-CoV-2 may be leveraging the protease network responsible for ENaC cleavage.

A 160-dimensional vector space (20 amino acids×8 positions on the peptide) was created for assessment of cleavage similarities between the 178 human proteases with biochemical validation from the MEROPS database[15]. FURIN (PCSK3) had overall proteolytic similarity to select PCSK family members, specifically PCSK5 (0.99), PCSK7 (0.99), PCSK6 (0.99), PCSK4 (0.98), and PCSK2 (0.94) (Table 2). It is also known that the protease PLG cleaves the ɣ-subunit of ENaC (ENaC-ɣ)[16].

TABLE 2

Protease cleavage propensities for FURIN and the other proteases identified as similar from the vector space analysis conducted. Similarity (FURIN) ranges from 0 to 1. Amino acids occuring in greater than 10% of the cleaved substrates at that position are in bold (compiled from MEROPS).

| Protease | Cleavage substrates | Similarity (FURIN) | P4 | P3 | P2 | P1 | P1' | P2' | P3' | P4' |
|---|---|---|---|---|---|---|---|---|---|---|
| MIMICKED PEPTIDE | | | R | R | A | R | S | V | A | S |
| FURIN | 208 | 1.00 | R(158) | K(34) | K(88) | R(203) | S(57) | V(46) | S(30) | S(19) |
| | | | I(8) | S(27) | R(68) | K(4) | A(23) | A(34) | G(21) | G(19) |
| | | | K(7) | R(26) | P(9) | L(1) | D(22) | L(31) | D(18) | A(17) |
| | | | F(7) | T(18) | A(8) | | E(20) | I(15) | E(16) | E(16) |
| | | | Others (26) | Others (97) | Others (34) | | Others (86) | Others (76) | Others (113) | Others (129) |
| PCSK5 | 129 | 0.992 | R(97) | K(23) | K(59) | R(125) | S(37) | V(25) | S(15) | E(15) |
| | | | K(8) | S(16) | R(41) | K(4) | A(11) | A(24) | G(15) | L(13) |
| | | | I(6) | R(13) | P(8) | | D(11) | L(22) | D(15) | P(12) |
| | | | V(4) | Q(10) | S(4) | | F(9) | I(12) | E(13) | G(11) |
| | | | Others (12) | Others(62) | Others (12) | | Others (58) | Others (43) | Others (62) | Others(71) |
| PCSK4 | 103 | 0.99 | R(77) | K(18) | K(49) | R(100) | S(31) | V(25) | S(13) | E(13) |
| | | | K(8) | R(12) | R(32) | K(3) | E(9) | A(19) | G(12) | P(11) |
| | | | V(4) | S(11) | P(6) | | D(9) | L(15) | D(12) | L(11) |
| | | | I(2) | Q(10) | A(3) | | A(9) | T(10) | E(11) | S(8) |
| | | | Others (7) | Others (45) | Others (7) | | Others (37) | Others (26) | Others (47) | Others (52) |
| PCSK6 | 105 | 0.99 | R(85) | K(19) | K(53) | R(102) | S(33) | V(29) | G(15) | E(13) |
| | | | K(7) | S(12) | S(36) | K(3) | A(10) | A(20) | S(14) | L(12) |
| | | | V(4) | R(12) | R(6) | | E(9) | L(15) | D(13) | P(11) |
| | | | I(2) | Q(10) | Q(3) | | D(9) | T(10) | E(11) | S(10) |
| | | | Others (7) | Others (45) | Others (7) | | Others (41) | Others (28) | Others (49) | Others (46) |
| PCSK7 | 117 | 0.989 | R(85) | K(23) | K(54) | R(112) | S(34) | V(25) | D(14) | E(15) |
| | | | K(9) | S(13) | R(38) | K(4) | E(11) | L(22) | S(13) | P(11) |
| | | | I(5) | R(12) | P(7) | | D(10) | A(20) | G(13) | L(11) |
| | | | V(4) | Q(11) | A(3) | | A(10) | T(11) | E(13) | A(10) |
| | | | Others (8) | Others (50) | Others (8) | | Others (44) | Others (31) | Others(52) | Others (60) |
| PCSK2 | 205 | 0.941 | R(86) | Q(27) | K(123) | R(192) | S(43) | V(27) | G(31) | E(31) |
| | | | K(13) | S(22) | R(44) | K(11) | Y(25) | G(23) | E(27) | D(27) |
| | | | V(11) | K(20) | P(9) | S(1) | A(20) | L(22) | S(17) | F(17) |
| | | | I(11) | E(19) | A(6) | F(1) | G(15) | A(22) | Q(17) | S(17) |
| | | | Others (8) | Others (109) | Others (9) | | Others (93) | Others (102) | Others(103) | Others (117) |
| PLG | 126 | | P(18) | R(17) | L(15) | R(65) | S(23) | R(13) | S(13) | G(12) |
| | | | A(16) | S(12) | S(13) | K(57) | A(20) | V(12) | P(11) | P(11) |
| | | | R(13) | Q(11) | P(12) | Others (3) | G(11) | S(12) | A(9) | L(11) |
| | | | S(8) | G(10) | A(11) | | R(10) | K(8) | Q(8) | A(9) |
| | | | Others (52) | Others (70) | Others (72) | | Others (51) | Others (70) | Others (74) | Others (72) |

Figure 8:
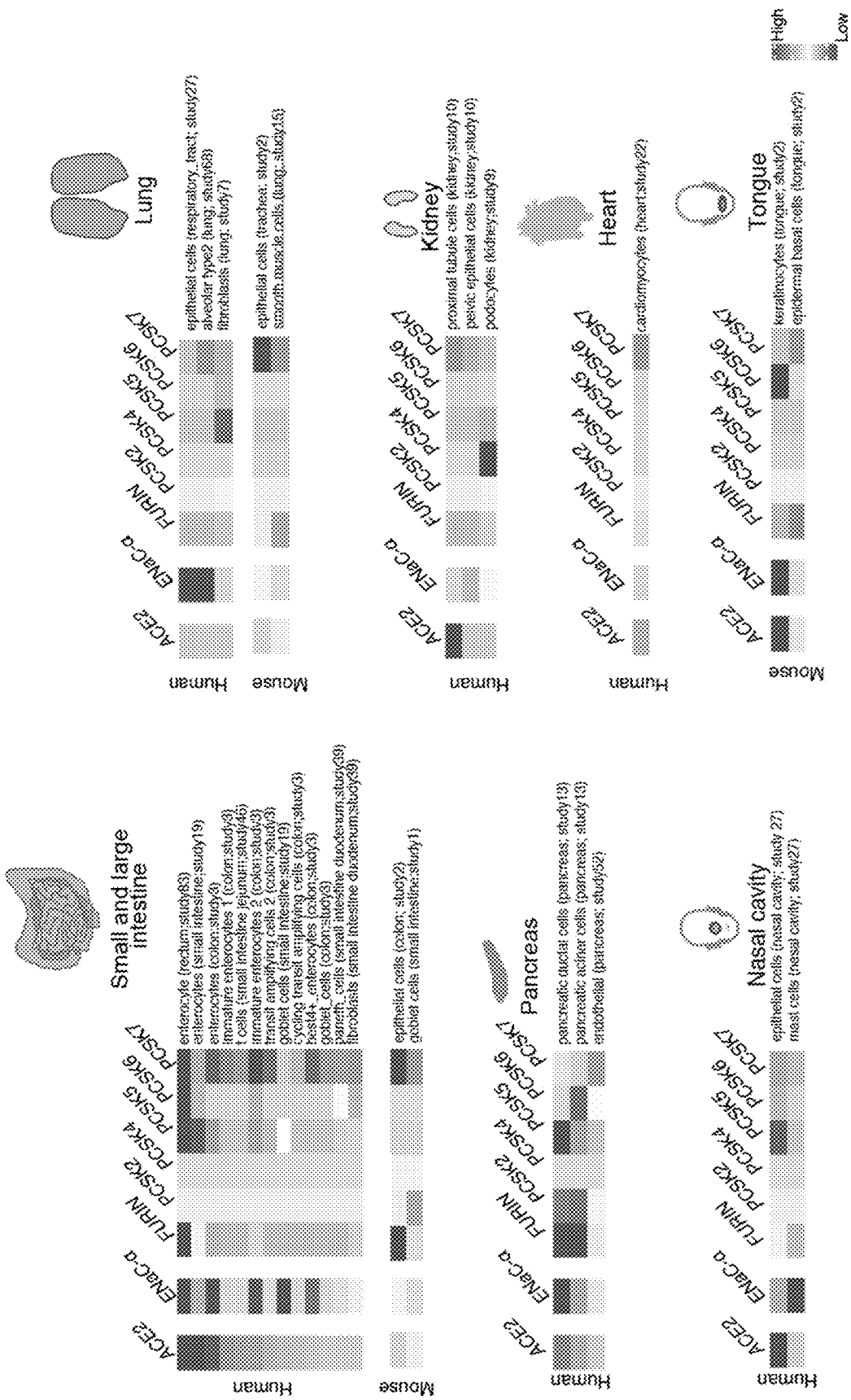
FIG. 8 depicts expression profiling of identified proteases. The heatmap depicts the relative expression of ACE2 and ENaC-α along with all the proteases that can potentially cleave the S1/S2 site. The relative expression levels are denoted on a scale of blue (low) to red (high). The rows denote proteases and columns denote cell-types.

The tissue tropism of SARS-CoV-2, in view of the cleavage similarities found within the host proteolytic network, the co-expression of these proteases concomitant with the viral receptor ACE2, and ENaC-α was assessed (FIG. 8). FURIN was expressed with ACE2 and ENaC-α in the colon (immature enterocytes, transit amplifying cells) and pancreas (ductal cells, acinar cells) of human tissues, as well as tongue (keratinocytes) of mouse tissues. PCSK5 and PCSK7 were broadly expressed across multiple cell types with ACE2 and ENaC-α, suggesting they are broad-spectrum proteases that cleave the S1/S2 site and further infection by the SARS-CoV-2 viral particle. In humans, concomitant with ACE2 and ENaC-α, PCSK6 appeared to be expressed in cells from the intestines, pancreas, and lungs, whereas PCSK2 was noted to be co-expressed in the respiratory tract and the pancreas (FIG. 8). Notably, extracellular proteases need not necessarily be expressed in the same cells as ACE2 and ENaC-α. Among the PCSK family members with the potential to cleave the mimicked 8-mer peptide, the same tissue can house multiple proteases. Also multiple tissues can share the same set of proteases. Redundancy may be wired into the mechanisms of host proteolytic activation of SARS-CoV-2, and may inform the development of selective human protease inhibitors as COVID-19 therapeutics.

The mimicry of a cleavable host peptide central to cardiovascular, renal, and pulmonary function provides a further strategy for the treatment and/or prevention of viral infection.

Example 2: Methods

Alignment of Coronavirus Spike Proteins

The complete S-protein sequence for SARS-CoV (Uniprot ID: P59594) and SARS-CoV-2 was obtained from uniprot (ftp.uniprot.org/pub/databases/uniprot/pre_release)[16]. Sequence alignments using Clustal-W, and comparison of SARS-CoV-2 versus other coronavirus strains were performed using JalView[17].

8-mer Analysis of Human Proteome

The number of 8-mers in Uniprot 20,350 reference sequences are 10,257,893 (10.26M). The previously identified SARS-CoV-2 8-mer 'RRARSVAS' was found in a Uniprot reference sequence (p-value≈$10.26M/20^8$=4E-4; chance of finding that particular 8-mer anywhere in the reference sequences).

Scoring Cleavage Sites

Biochemical specificities are inferred from substrates of the proteases that have been determined using the evidence from (i) N-terminal sequencing, (ii) mass spectroscopy, (iii) mutational studies, (iv) consensus analysis or (v) liquid chromatography. The protein residues from the protease substrates spanning the scissile bond (±4 residues) is considered to define sequence specificity of the motif. The motif length thus spans across 8 residues (or positions), and frequency of all the 20 amino acids at each position is calculated from the substrates identified for each of the proteases to get a position frequency matrix (PFM, with a dimension of 8×20). This PFM was converted to a probability matrix by normalizing to the frequency distribution of all the 20 amino acids per position. The position frequency matrices were downloaded from the MEROPS database[15]. In total, probabilities matrices for 178 proteases were constructed. The number of distinct cleavages for each protease ranges from as few as 10 to over 3000, based on which probability matrices for the cleavage of the 8-mer polypeptide was estimated (Table 2). The probability matrix is then used to scan the peptide sequence ('RRARSVAS') using a window frame equal to the length of the motif. A log-likelihood ratio score is calculated for each sequence position in the scanned window with respect to background distribution of particular amino acid in the human proteome and summed up across all the positions to get a motif score. A random set of sequences are generated from the given background of amino acid distribution in the human proteome and used as a null model to evaluate the statistical significance of the scanned window. FIMO tool was used to obtain the scores and the corresponding statistical significance of the PWM match[18]. These were then used to estimate cleavage propensity by assuming background distribution of amino-acid frequencies from human proteome[19] using MEME[20] and FIMO[18]. A stringent cut-off of 1E-04 was used to identify the potential cleavage sites on S proteins of both SARS-CoV and SARS-CoV-2 at S1/S2 site. The hits obtained were further manually filtered to ensure that residue at the immediate vicinity of cleavage site is conserved.

Calculating the Cosine Similarity Metric for Protease Cleavage Site

The position frequency matrix (PFM) of the individual proteases obtained from the MEROPS database was converted to a probability weight matrix (PWM) (normalized and scaled). Out of 178 proteases, there were 146 proteases that had specificity information available on the 8 mer peptide spanning the cleavage site (±4). The 20 (amino acids)×8 (position) matrix defined for each of the proteases were flattened into a single vector with 160 elements. A cosine similarity calculation was performed between all pairs (X,Y) of protease specificity vector. The similarity was derived as the normalized dot product of X and Y: K(X, Y)=<X, Y>/(||X||*||Y||)).

Overlap of Cell Types Expressing ENaC-α, ACE2 and Proteases from scRNA-seq Datasets A systematic expression profiling of the ACE2 and ENaC-α was performed across 65 published human and mouse single-cell studies comprising ~1.3 million cells using nferX Single Cell platform (Table 3, academia.nferx.com)[6]. The ACE2 expression could be detected in 67 studies (59 studies of human samples and 8 studies of mouse samples) spanning across ~50 tissues, over 450 cell-types and ~1.05 million cells. In order to call a given cell-type to be positive for both ACE2 and a protease we applied a cutoff of 1% of the cells in the total cell-type cluster population to have a non-zero count associated with both ACE2 and the respective protease. The mean expression of the proteases, ENaC-α and ACE2 was derived for individual cell population within each of the studies. The cell-type information was obtained from the author annotations provided for each of the studies. The analysis was performed separately on the mouse and human datasets. For each protease, the mean expression of in a given cell-population (mean log[cp10k+1] counts) was Z-score normalized (to ensure the sd=1 and mean -0 for all the genes) to obtain relative expression profiles across all the samples. The same normalization was applied to ACE2 and ENaC-α and both human and mouse datasets were analyzed independently by generating heatmaps. The cell types having zero-expression values of ACE2 were also included as negative control to probe the expression of various proteases.

TABLE 3

List of single-cell studies analyzed and incorporated into the nferX resource (https://academia.nferx.com/)

| Study ID | Organism | Study Title | Pubmed ID (PMID) |
|---|---|---|---|
| study1 | *Mus musculus* | A single-cell survey of the small intestinal epithelium | PMID: 29144463 |
| study2 | *Mus musculus* | Single-cell transcriptomics of 20 mouse organs creates a Tabula Muris. | PMID: 30283141 |
| study3 | *Homo sapiens* | Intra- and Inter-cellular Rewiring of the Human Colon during Ulcerative Colitis | PMID: 31348891 |
| study4 | *Homo sapiens* | Immune Cell Atlas: Blood Mononuclear Cells (2 donors, 2 sites) | singlecell.broadinstitute.org/single_cell/study/SCP345/ica-blood-mononuclear-cells-2-donors-2-sites |
| study5 | *Homo sapiens* | Spleen - Ischaemic sensitivity of human tissue by single cell RNA seq | data.humancellatlas.org/explore/projects/c4077b3c-5c98-4d26-a614-246d12c2e5d7 |
| study6 | *Homo sapiens* | Esophagus - Ischaemic sensitivity of human tissue by single cell RNA seq | data.humancellatlas.org/explore/projects/c4077b3c-5c98-4d26-a614-246d12c2e5d7 |
| study7 | *Homo sapiens* | A cellular census of human lungs identifies novel cell states in health and in asthma. | PMID: 31209336 |
| study8 | *Mus musculus* | A revised airway epithelial hierarchy includes CFTR-expressing ionocytes | PMID: 30069044 |
| study9 | *Homo sapiens* | Fetal Kidney - Spatiotemporal immune zonation of the human kidney | PMID: 31604275 |
| study10 | *Homo sapiens* | Mature Kidney - Spatiotemporal immune zonation of the human kidney | PMID: 31604275 |

TABLE 3-continued List of single-cell studies analyzed and incorporated into the nferX resource (https://academia.nferx.com/)

| Study ID | Organism | Study Title | Pubmed ID (PMID) |
| --- | --- | --- | --- |
| study11 | *Homo sapiens* | Identification of grade and origin specific cell populations in serous epithelial ovarian cancer by single cell RNA-seq | PMID: 30383866 |
| study12 | *Homo sapiens* | A human liver cell atlas reveals heterogeneity and epithelial progenitors. | PMID: 31292543 |
| study13 | *Homo sapiens* | Human Pancreas scRNA-seq (Integration of 3 Datasets) | PMID: 27345837, PMID: 27667667, PMID: 27693023 |
| study14 | *Homo sapiens* | Census Of Immune Cells | data.humancellatlas.org/explore/projects/cc95ff89-2e68-4a08-a234-480eca21ce79 |
| study15 | *Mus musculus* | Mapping the Mouse Cell Atlas by Microwell-Seq. | PMID: 29474909 |
| study16 | Homo sapiens | Transcriptome Landscape of Human Folliculogenesis Reveals Oocyte and Granulosa Cell Interactions. | PMID: 30472193 |
| study17 | *Homo sapiens* | A Cellular Anatomy of the Normal Adult Human Prostate and Prostatic Urethra. | PMID: 30566875 |
| study18 | *Homo sapiens* | Single-cell reconstruction of the early maternalâ€"fetal interface in humans | PMID: 30429548 |
| study19 | *Homo sapiens* | Single-cell transcriptome analysis reveals differential nutrient absorption functions in human intestine | PMID: 31753849 |
| study20 | *Homo sapiens* | Single-Cell Transcriptomic Analysis of Primary and Metastatic Tumor Ecosystems in Head and Neck Cancer | PMID: 29198524 |
| study21 | *Homo sapiens* | Single-cell transcriptomic atlas of the human retina identifies cell types associated with age-related macular degeneration | PMID: 31653841 |
| study22 | *Homo sapiens* | Single-cell reconstruction of the adult human heart during heart failure and recovery reveals the cellular landscape underlying cardiac function | PMID: 31915373 |
| study23 | *Mus musculus* | Single cell analysis reveals immune cell-adipocyte crosstalk regulating the transcription of thermogenic adipocytes | PMID: 31644425 |
| study24 | *Mus musculus* | An atlas of the aging lung mapped by single cell transcriptomics and deep tissue proteomics | PMID: 30814501 |
| study25 | *Homo sapiens* | The adult human testis transcriptional cell atlas | PMID: 30315278 |
| study26 | *Homo sapiens* | Single-cell reconstruction of follicular remodeling in the human adult ovary | PMID: 31320652 |
| study27 | *Homo sapiens* | Single-cell analysis of olfactory neurogenesis and differentiation in adult humans | PMID: 32066986 |
| study28 | *Homo sapiens* | Single-Cell Transcriptomic Map of the Human and Mouse Bladders | PMID: 31462402 |
| study29 | *Mus musculus* | Single cell analysis reveals immune cell-adipocyte crosstalk regulating the transcription of thermogenic adipocytes | PMID: 31644425 |
| study30 | *Homo sapiens* | Single-cell analysis of human adipose tissue identifies depot- and disease-specific cell types | PMID: 32066997 |
| study31 | *Homo sapiens* | Adipose tissue - Construction of a human cell landscape at single-cell level | www.nature.com/articles/s41586-020-2157-4 |
| study32 | *Homo sapiens* | Adrenal gland - Construction of a human cell landscape at single-cell level | www.nature.com/articles/s41586-020-2157-4 |
| study33 | *Homo sapiens* | Artery - Construction of a human cell landscape at single-cell level | www.nature.com/articles/s41586-020-2157-4 |
| study34 | *Homo sapiens* | Ascending colon - Construction of a human cell landscape at single-cell level | www.nature.com/articles/s41586-020-2157-4 |
| study35 | *Homo sapiens* | Bladder - Construction of a human cell landscape at single-cell level | www.nature.com/articles/s41586-020-2157-4 |

TABLE 3-continued

List of single-cell studies analyzed and incorporated into the nferX resource (https://academia.nferx.com/)

| Study ID | Organism | Study Title | Pubmed ID (PMID) |
| --- | --- | --- | --- |
| study36 | Homo sapiens | Bone marrow - Construction of a human cell landscape at single-cell level | www.nature.com/articles/s41586-020-2157-4 |
| study37 | Homo sapiens | Cerebellum - Construction of a human cell landscape at single-cell level | www.nature.com/articles/s41586-020-2157-4 |
| study38 | Homo sapiens | Cervix - Construction of a human cell landscape at single-cell level | www.nature.com/articles/s41586-020-2157-4 |
| study39 | Homo sapiens | Small intestine duodenum - Construction of a human cell landscape at single-cell level | www.nature.com/articles/s41586-020-2157-4 |
| study40 | Homo sapiens | Appendix - Construction of a human cell landscape at single-cell level | www.nature.com/articles/s41586-020-2157-4 |
| study41 | Homo sapiens | Esophagus - Construction of a human cell landscape at single-cell level | www.nature.com/articles/s41586-020-2157-4 |
| study42 | Homo sapiens | Fallopian tube - Construction of a human cell landscape at single-cell level | www.nature.com/articles/s41586-020-2157-4 |
| study43 | Homo sapiens | Gallbladder - Construction of a human cell landscape at single-cell level | www.nature.com/articles/s41586-020-2157-4 |
| study44 | Homo sapiens | Heart - Construction of a human cell landscape at single-cell level | www.nature.com/articles/s41586-020-2157-4 |
| study45 | Homo sapiens | Small intestine ileum - Construction of a human cell landscape at single-cell level | www.nature.com/articles/s41586-020-2157-4 |
| study46 | Homo sapiens | Small intestine jejunum - Construction of a human cell landscape at single-cell level | www.nature.com/articles/s41586-020-2157-4 |
| study47 | Homo sapiens | Kidney - Construction of a human cell landscape at single-cell level | www.nature.com/articles/s41586-020-2157-4 |
| study48 | Homo sapiens | Liver - Construction of a human cell landscape at single-cell level | www.nature.com/articles/s41586-020-2157-4 |
| study49 | Homo sapiens | Lung - Construction of a human cell landscape at single-cell level | www.nature.com/articles/s41586-020-2157-4 |
| study50 | Homo sapiens | Muscle - Construction of a human cell landscape at single-cell level | www.nature.com/articles/s41586-020-2157-4 |
| study51 | Homo sapiens | Omental adipose tissue - Construction of a human cell landscape at single-cell level | www.nature.com/articles/s41586-020-2157-4 |
| study52 | Homo sapiens | Pancreas - Construction of a human cell landscape at single-cell level | www.nature.com/articles/s41586-020-2157-4 |
| study53 | Homo sapiens | Peripheral blood - Construction of a human cell landscape at single-cell level | www.nature.com/articles/s41586-020-2157-4 |
| study54 | Homo sapiens | Lung pleura - Construction of a human cell landscape at single-cell level | www.nature.com/articles/s41586-020-2157-4 |
| study55 | Homo sapiens | Prostate - Construction of a human cell landscape at single-cell level | www.nature.com/articles/s41586-020-2157-4 |
| study56 | Homo sapiens | Rectum - Construction of a human cell landscape at single-cell level | www.nature.com/articles/s41586-020-2157-4 |
| study57 | Homo sapiens | Sigmoid colon - Construction of a human cell landscape at single-cell level | www.nature.com/articles/s41586-020-2157-4 |
| study58 | Homo sapiens | Spleen - Construction of a human cell landscape at single-cell level | www.nature.com/articles/s41586-020-2157-4 |
| study59 | Homo sapiens | Stomach - Construction of a human cell landscape at single-cell level | www.nature.com/articles/s41586-020-2157-4 |
| study60 | Homo sapiens | Brain temporal lobe - Construction of a human cell landscape at single-cell level | www.nature.com/articles/s41586-020-2157-4 |
| study61 | Homo sapiens | Thyroid - Construction of a human cell landscape at single-cell level | www.nature.com/articles/s41586-020-2157-4 |
| study62 | Homo sapiens | Trachea - Construction of a human cell landscape at single-cell level | www.nature.com/articles/s41586-020-2157-4 |
| study63 | Homo sapiens | Transverse colon - Construction of a human cell landscape at single-cell level | www.nature.com/articles/s41586-020-2157-4 |
| study64 | Homo sapiens | Ureter - Construction of a human cell landscape at single-cell level | www.nature.com/articles/s41586-020-2157-4 |
| study65 | Homo sapiens | Uterus - Construction of a human cell landscape at single-cell level | www.nature.com/articles/s41586-020-2157-4 |

An analysis to identify the cell types with significant overlap of ACE2 and ENaC-α expression was performed. To this end, cell types in which ENaC-α is expressed in a significantly higher proportion of ACE2-expressing cells than in the overall population of cells of that sub-type were shortlisted. The ratios of these proportions were computed, and a corresponding Fisher exact test was used to compute significance.

REFERENCES

1. Walls, A. C. et al. Structure, Function, and Antigenicity of the SARS-CoV-2 Spike Glycoprotein. Cell (2020) doi: 10.1016/j.cell.2020.02.058.
2. Belouzard, S., Chu, V. C. & Whittaker, G. R. Activation of the SARS coronavirus spike protein via sequential proteolytic cleavage at two distinct sites. Proceedings of the National Academy of Sciences 106, 5871-5876 (2009).
3. Belouzard, S., Millet, J. K., Licitra, B. N. & Whittaker, G. R. Mechanisms of Coronavirus Cell Entry Mediated by the Viral Spike Protein. Viruses 4, 1011-1033 (2012).
4. Elbe, S. & Buckland-Merrett, G. Data, disease and diplomacy: GISAID's innovative contribution to global health: Data, Disease and Diplomacy. Global Challenges 1, 33-46 (2017).
5. Carrillo-Tripp, M. et al. VIPERdb2: an enhanced and web API enabled relational database for structural virology. Nucleic Acids Research 37, D436—D442 (2009).
6. Rossier, B. C., Baker, M. E. & Studer, R. A. Epithelial Sodium Transport and Its Control by Aldosterone: The Story of Our Internal Environment Revisited. Physiological Reviews 95, 297-340 (2015).
7. Noreng, S., Bharadwaj, A., Posert, R., Yoshioka, C. & Baconguis, I. Structure of the human epithelial sodium channel by cryo-electron microscopy. Elife 7, (2018).
8. Hughey, R. P., Bruns, J. B., Kinlough, C. L. & Kleyman, T. R. Distinct pools of epithelial sodium channels are expressed at the plasma membrane. J. Biol. Chem. 279, 48491-48494 (2004).
9. Hughey, R. P. et al. Epithelial sodium channels are activated by furin-dependent proteolysis. J. Biol. Chem. 279, 18111-18114 (2004).
10. Welzel, M. et al. Five novel mutations in the SCNN1A gene causing autosomal recessive pseudohypoaldosteronism type 1. European Journal of Endocrinology 168, 707-715 (2013).
11. Venkatakrishnan, A. et al. Knowledge synthesis from 100 million biomedical documents augments the deep expression profiling of coronavirus receptors. http://biorxiv.org/lookup/doi/10.1101/2020.03.24.005702 (2020) doi:10.1101/2020.03.24.005702.
12. Shweta, F. et al. Augmented Curation of Unstructured Clinical Notes from a Massive EHR System Reveals Specific Phenotypic Signature of Impending COVID-19 Diagnosis. http://medrxiv.org/lookup/doi/10.1101/2020.04.19.20067660 (2020) doi:10.1101/2020.04.19.20067660.
13. Butterworth, M. B. Regulation of the epithelial sodium channel (ENaC) by membrane trafficking. Biochimica et Biophysica Acta (BBA)—Molecular Basis of Disease 1802, 1166-1177 (2010).
14. Musante, I. et al. Peripheral localization of the epithelial sodium channel in the apical membrane of bronchial epithelial cells. Exp Physiol 104, 866-875 (2019).
15. Rawlings, N. D. et al. The MEROPS database of proteolytic enzymes, their substrates and inhibitors in 2017 and a comparison with peptidases in the PANTHER database. Nucleic Acids Research 46, D624—D632 (2018).
16. Passero, C. J. et al. Plasmin Activates Epithelial Na+ Channels by Cleaving the γ Subunit. J. Biol. Chem. 283, 36586-36591 (2008).

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

---

What is claimed is:

1. A method of treating or reducing viral infection in a human subject, comprising administering to the human subject a pharmaceutical composition comprising a protease inhibitor and Proprotein Convertase Subtilisin/Kexin Type 2 (PCSK2), wherein the protease inhibitor prevents a protease from cleaving a peptide at a cleavage site, wherein the cleavage site results in mimicry of a peptide on the human epithelial sodium channel α-subunit (ENaC-α).

2. The method of claim 1, wherein the pharmaceutical composition further comprises an inhibitor of Furin, Proprotein Convertase Subtilisin/Kexin Type 4 (PCSK4), Proprotein Convertase Subtilisin/Kexin Type 5 (PCSK5), Proprotein Convertase Subtilisin/Kexin Type 6 (PCSK6), Proprotein Convertase Subtilisin/Kexin Type 7 (PCSK7), Plasminogen (PLG), or any combination thereof.

3. The method of claim 1, wherein the composition is administered to the human subject directly to an organ selected from lung, small intestine, large intestine, pancreas, kidney, hemi, or tongue.

4. The method of claim 1, wherein the composition is administered to the human subject directly to the nasopharynx and/or the oropharynx.

5. The method of claim 1, wherein the composition is administered subcutaneously, intravenously, intramuscularly, intranasally, by inhalation, orally, sublingually, by buccal administration, topically, transdermally, or transmucosally.

6. The method of claim 1, wherein the human subject is suffering from SARS-COV-2 infection.

* * * * *